United States Patent [19]
Spence et al.

[11] Patent Number: 6,019,722
[45] Date of Patent: Feb. 1, 2000

[54] DEVICE TO PERMIT OFFPUMP BEATING HEART CORONARY BYPASS SURGERY

[75] Inventors: Paul A. Spence, Louisville, Ky.; Warren Williamson, IV, Loveland, Ohio

[73] Assignee: Guidant Corporation, Menlo Park, Calif.

[21] Appl. No.: 08/936,184

[22] Filed: Sep. 17, 1997

[51] Int. Cl.[7] .................................................. A61B 17/01
[52] U.S. Cl. .......................... 600/210; 600/201; 600/204; 600/214; 600/227; 600/228; 600/229; 600/231; 600/232; 600/235; 600/37
[58] Field of Search .................................. 600/201, 204, 600/205, 206, 208, 210, 214, 227, 228, 229, 231, 232, 233, 235, 37

[56] References Cited

U.S. PATENT DOCUMENTS

| | | | |
|---|---|---|---|
| 2,082,782 | 6/1937 | Allen | 600/205 |
| 4,217,890 | 8/1980 | Owens . | |
| 4,457,300 | 7/1984 | Budde | 600/228 |
| 4,637,377 | 1/1987 | Loop | 600/37 |
| 4,852,552 | 8/1989 | Chaux | 600/232 |
| 4,957,477 | 9/1990 | Lundback . | |
| 5,131,905 | 7/1992 | Grooters . | |
| 5,139,517 | 8/1992 | Corral . | |
| 5,150,706 | 9/1992 | Cox et al. | 600/37 X |
| 5,256,132 | 10/1993 | Snyders | 600/37 X |
| 5,453,078 | 9/1995 | Valentine et al. . | |
| 5,480,425 | 1/1996 | Ogilive . | |
| 5,509,890 | 4/1996 | Kazama . | |
| 5,727,569 | 3/1998 | Benetti et al. . | |
| 5,730,757 | 3/1998 | Benetti et al. | 606/198 |
| 5,782,746 | 7/1998 | Wright | 600/37 |
| 5,807,243 | 9/1998 | Vierra et al. | 128/898 |

FOREIGN PATENT DOCUMENTS

| | | |
|---|---|---|
| 0 791 330 A2 | 8/1997 | European Pat. Off. . |
| 97/40738 | 11/1997 | WIPO . |

*Primary Examiner*—Jeffrey A. Smith
*Attorney, Agent, or Firm*—Terry M. Gernstein

[57] ABSTRACT

A heart retractor links lifting of the heart and regional immobilization which stops one part of the heart from moving to allow expeditious suturing while permitting other parts of the heart to continue to function whereby coronary surgery can be performed on a beating heart while maintaining cardiac output unabated and uninterrupted. Circumflex coronary artery surgery can be performed using the heart retractor of the present invention. The retractor includes a plurality of flexible arms and a plurality of rigid arms as well as a surgery target immobilizing element. One form of the retractor can be used in minimally invasive surgery, while other forms of the retractor can accommodate variations in heart size and paracardial spacing.

42 Claims, 11 Drawing Sheets

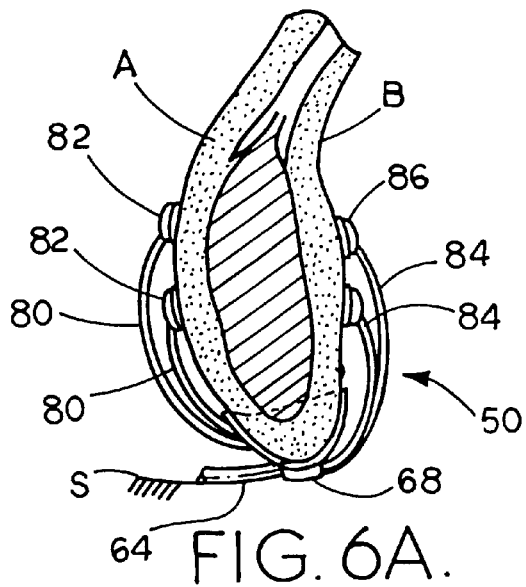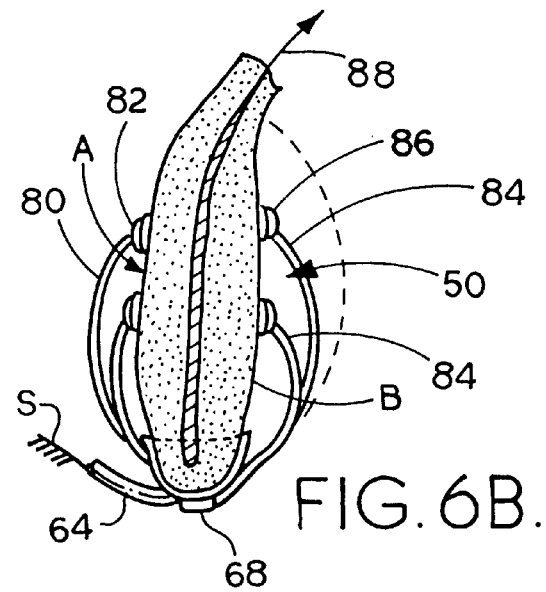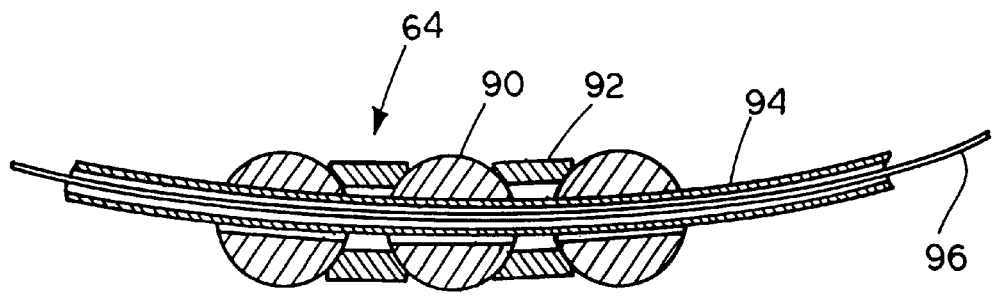

DEVICE TO PERMIT OFFPUMP BEATING HEART CORONARY BYPASS SURGERY

TECHNICAL FIELD OF THE INVENTION

The present invention relates to the general art of cardiac surgery, and to the particular field of heart retractors used in cardiac surgery.

BACKGROUND OF THE INVENTION

There are as many as 300,000 coronary bypass graft procedures performed annually in the United States. Each of those procedures may include one or more graft vessels. Currently, each graft vessel must be hand sutured. As many as four or more grafts are placed in a procedure. Until recently, coronary artery bypass procedures have been performed with the patient on cardiopulmonary bypass whereby the heart is stopped with cardioplegia and the surgery performed on an exposed and still heart.

Some pioneering surgeons are performing procedures in which the coronary bypass is performed on a beating heart. That is, without heart-lung bypass and cardioplegia. This minimizes the time it takes to perform the procedure and reduces the cost of the operation by eliminating the heart-lung bypass machine.

Coronary Artery Bypass Grafting (CABG) is performed and a new blood supply to the heart muscle is established when coronary arteries are blocked with calcium or plaque. A new blood supply conduit is joined to the diseased coronary, distal to the blockage, thus providing a fresh supply of oxygenated blood to the vessel in question. Today, this is accomplished by hand suturing a graft vessel (the new supply of blood) to the diseased vessel. This junction is called an anastomosis of vessels. Many different types of supply conduits can be used. Examples are cadaver vein, saphenous vein, radial artery, internal mammary artery, and the like.

By way of background, the basic operation of a heart will be briefly discussed. The heart works like a pump. The left and right ventricles are separate but share a common wall (the septum). The left ventricle is thicker and pumps the blood into the systemic circulation. The work it performs is much greater than the right ventricle. The right ventricle pumps blood into the pulmonary circulation, which is a low pressure circuit. The left ventricle wall (a low energy system) is much thinner than the right ventricle.

The left ventricle fills in diastole and ejects in systole. The difference between the diastolic volume (largest) and the systolic volume (smallest) (the stroke volume or amount of blood ejected on each heartbeat) multiplied by heart rate determines the cardiac output of the heart (liters/min. of flow). The heart shortens during systole as the muscle contracts. There are a number of motions during contraction (including a considerable amount of rotation) but for practical purposes the heart can be thought of as a truncated cone. Shortening occurs along its length and also along its diameter. For purposes of this disclosure, the more important of the two motions is the shortening along the diameter since the ejection volume varies as the square vs. along the length which varies with the first power.

The heart functions well whether the person is upright, upside down, prone or supine. It sits inside the pericardium—a sac which limits its motion and spreads the support on the heart so that no matter how a person positions himself, it is not particularly compressed and is able to fill and then eject with each heartbeat. The concept of the pericardium spreading the load is critical, i.e., when lying supine, the posterior pericardium supports the heart over a large surface of the heart just as when the person is lying on his stomach, the front of the pericardium spreads the load.

When the chest is opened by a median sternotomy it is possible to gain access to all chambers and surfaces of the heart. This combined with the fact that this incision is usually less painful than a thoracotomy (rib separation), makes this the preferred surgical approach to the heart.

The coronary vessels are surface vessels, only occasionally dipping into the myocardium making them accessible without opening the heart. Traditionally, bypass surgery is done with the heart arrested. This stops the motion of the heart and allows the arrest of the coronary circulation so the surgeon sews in a bloodless and easy to see field. Since the heart is stopped, the patient would suffer irreversible damage to the brain and other tissues and organs without the use of the heart-lung machine to support the general circulation. Although the heart-lung machine has been refined, it is particularly toxic to older and debilitated patients and it is expensive.

It is possible to perform surgery off bypass, while the heart is beating and the coronaries are under positive blood pressure; however, there may be problems. One problem is that not all vessels are accessible since some vessels are on the posterior or inferior surfaces and that when such vessels are brought into view by lifting the heart, cardiac performance is impaired such that the cardiac output falls and blood pressure drops. A second problem is that the heart moves so that suturing in vessels (12 to 15 stitches in a vessel under 2 mm in diameter) might be inaccurate and a third problem is that there is blood in the field as the coronary circulation is not interrupted. This last problem is now largely solved by snares, which temporarily stop the flow of blood through the targeted arteries. The problem of lifting the heart is not to impair the performance of the heart while at the same time adequately exposing the heart and regionally immobilizing the vessel during beating heart surgery, and this problem is not solved with any prior art system.

Therefore there is a significant need for a means and a method for lifting a heart so as not to impair the performance of the heart while at the same time adequately exposing the heart and regionally immobilizing a vessel during beating heart surgery.

Lifting of the heart is deleterious to heart function for several reasons. First, the lifting of the heart impairs the venous return to the heart so that there is less diastolic filling of the heart (this can largely be corrected by putting the head down and the feet up to increase venous return). Second, the heart is distorted. Using a hand or spatula to lift the heart is quite different than simply changing body position when the heart is inside the chest. The force of the hand on the heart is localized so that the heart is no longer a truncated cone, but is much flatter. This shape is much less effective for ejection (the circle is the most effective as it has the highest ratio of volume to diameter) and flattening also limits the diastolic volume so that inadequate filling occurs.

In order to perform cardiac surgery on a beating heart, there is a need to lift, support and orient the heart without reducing its ability to function. The inventors have discovered that the secret is to work like the pericardium does when a person changes body position and do everything possible to keep the heart's shape consistent.

In coronary bypass operations, grafts have to be anastomosed to the anterior descending artery (right coronary artery branch), the circumflex artery, and to the posterior descending artery. The anterior descending artery lies on the front surface of the heart and is easily accessible to the surgeon without particular help from surgical assistants or using any devices. The circumflex and posterior descending arteries, however, lie on the back surface of the heart. Therefore, to expose the circumflex artery to a field of view of the surgeon, it is mandatory to lift the heart and rotate it about the axis of the inferior vena cava and the superior vena cava. Likewise, to expose the posterior descending artery, it is necessary to lift the heart and rotate it in the direction of its apex. If the heart is moved improperly, it may go into fibrillation.

Ordinarily, a surgical assistant is employed to lift the heart by using his or her hand, this is satisfactory for an arrested heart. However this is not satisfactory for a beating heart. However, it is very difficult and tiring to keep the heart in a steady position. Furthermore, the myocardium in contact with the assistant's fingers may be damaged by pressure, avulsion, and premature rewarming. Further, the assistant's hand in the operative field can get in the way, and the assistant, who often stands next to the surgeon may restrict the surgeon's movements.

Therefore, there is a need for a heart retractor which will support the heart in position for coronary bypass surgery of the circumflex coronary artery and posterior descending artery.

Another prior art method of supporting a heart is by use of a sling. A sling is a network of fabric or plastic that is placed around the heart in the manner of a hammock. The heart is then supported by the sling. It is noted that in order for a sling to work as a retractor, the surgeon is required to arrange the ties to be pulled from the proper direction, such as normal to the desired direction of lift, which can be onerous. This presents a serious problem since there are no easy reference points above the patient in which to attach these ties.

While the art has included several inventions intended to support the heart during coronary bypass surgery of the circumflex coronary artery, these inventions have several drawbacks that have hindered their acceptance in the art. For example, the use of nets to support the heart exposes the heart to fine stands which impinge on the heart and may cause damage. Furthermore, nets may impede the surgical target and require special techniques or procedures to remove the net from the surgical target area. This is especially onerous if the net mesh is fine. Flat cloth tapes are a form of net, and may damage the heart due to a rough texture of the cloth and the small area of contact between the tape strands and the heart. Further, tapes and similar devices that do not have large surface areas contacting the heart may not support the heart in a uniform manner and may create large pressure areas at the contact points.

Therefore, there is a need for a heart retractor which will support the heart in position for coronary bypass surgery of the circumflex coronary artery in a manner that tool not damage the heart yet will provide easy access to the surgical target and keeps working while cardiac output is maintained.

A further consideration in coronary artery surgery is hemorrhage from the incision into the coronary artery at the proposed anastomotic site. Therefore, heretofore, coronary artery surgery has been carried out under conditions of cardiac arrest and aortic root cross clamping. Hence, the myocardium is temporarily deprived of coronary blood supply. In some patients, an additional coronary blood supply, through the form of bronchial circulation, causes significant hemorrhage during the bypass grafting process. This hemorrhage is inconvenient, as it masks the surgeon's view during the delicate suturing process, and threatens the well-being of the patient. Performing surgery in this manner has several additional drawbacks, including the need to stop the heart, the need to insert special equipment and procedural steps to carry out the function of moving blood through the patient's body while the heart is stopped.

Therefore, there is a need for a heart retractor which will support the heart in position for coronary bypass surgery of all of the coronary arteries, including the circumflex coronary artery, in a manner such that the tool does not damage the heart while cardiac output is maintained yet will provide easy access to the surgical target and which can be used in a manner that does not require the heart to be stopped.

Still further, there is a need for a heart retractor which permits regional as well as specific immobilization of the heart.

However, the continued operation of the heart will produce problems, in addition to the above-discussed problems, of forming a moving target for the surgeon. That is, since the heart continues to beat during the operation, the surgical target will move in connection with such beating movement. The heart cannot be stopped or unduly constrained without increasing the danger of fibrillation.

Therefore, there is a need for a heart retractor which will support a beating heart in position for coronary bypass surgery of coronary arteries in a manner that will not damage the heart yet will provide specific and regional support while allowing unabated cardiac output.

Recently, there has been interest in minimally invasive coronary bypass surgery. This is not surprising since a median sternotomy and a run on the cardiopulmonary bypass pump are not well tolerated by some patients, combined with the added cost of coronary bypass equipment and staff. The procedure results in considerable recovery time and is associated with a risk of death and major complication. While the ultimate goal is to provide bypass to all vessels by port access (like gallbladder surgery) and to eliminate the need for cardiopulmonary bypass, a more limited but reasonable option for the next number or years will be to perform bypass off pump with an incision (sternotomy or thoracotomy). A tool which could allow performance of multivessel off pump bypass would be most helpful.

Therefore, there is a need for a heart retractor which will support the heart in position for minimally invasive coronary bypass surgery of coronary arteries, including the circumflex coronary artery, in a manner that will not damage the heart yet will provide easy access to the surgical target without requiring the heart to be stopped yet without unduly constraining the heart.

Still further, the inventors have observed that not all hearts are the same size, shape and have the same spacing between corresponding areas. Thus, while all hearts are basically the same, there may be a variation between individual hearts. Therefore, a device that supports a heart should account for these variations. This is especially true if the heart is to continue pumping during the operation and while it is supported. If the support is not fit to the particular heart, it may constrict the heart in some manner and thus interfere with the continued output of the heart.

Therefore, there is a need for a heart retractor which will support a heart, especially a beating heart, during coronary surgery and which can be adjusted to fit the particular needs of the individual heart and will support the heart both in gross and regionally.

OBJECTS OF THE INVENTION

It is main object of the present invention to provide a heart retractor which will support the weight of a beating heart and maintain cardiac output unabated and uninterrupted even though the heart is maintained in an unnatural position and/or orientation.

It is a further object of the present invention to provide a heart retractor which will support a beating heart in position for coronary bypass surgery and which supports the heart both regionally and in gross.

It is a further object of the present invention to provide a heart retractor which will support a beating heart in position for coronary bypass surgery and which supports the heart both regionally and in gross and which can account for variations in individual hearts.

It is a further object of the present invention to provide a heart retractor which will support a beating heart in position for coronary bypass surgery of the coronary arteries, including the circumflex coronary artery.

It is another object of the present invention to provide a heart retractor which will support the heart in position for coronary bypass surgery of the coronary arteries in a manner that will not damage the heart yet will provide easy access to the surgical target.

It is another object of the present invention to provide a heart retractor which will support the heart in position for coronary bypass surgery in a manner that will not damage the heart yet will provide easy access to the surgical target and which can be used in a manner that does not require the heart to be stopped.

It is another object of the present invention to provide a heart retractor which will support the heart in position for coronary bypass surgery in a manner that will not damage the heart yet will provide easy access to the surgical target without requiring the heart to be stopped yet without unduly constraining the heart.

It is another object of the present invention to provide a heart retractor which will support the heart in position for minimally invasive coronary bypass surgery in a manner that will not damage the heart yet will provide easy access to the surgical target without requiring the heart to be stopped yet without unduly constraining the heart.

It is another object of the present invention to provide a heart retractor which will provide regional and specific immobilization of the heart.

It is another object of the present invention to provide a heart retractor which will isolate one region of the heart while allowing cardiac output to be sustained.

SUMMARY OF THE INVENTION

These, and other, objects are achieved by a heart retractor which links lifting of the heart and regional immobilization which stops one location of the heart from moving while permitting the remainder of the heart to move in a normal manner. This provides a stationary target for the surgeon while supporting the heart in a safe manner and in a manner that does not interfere with the surgeon or his field of sight. In this manner, the retractor can be used to support a heart during cardiac coronary surgery without requiring an assistant to hold the heart, yet will permit the surgical procedure to be carried out without requiring cardiac arrest.

More specifically, a first form of the heart retractor includes an element that can be cup-shaped and that engages the apex portion of the heart being supported, as well as a plurality of support arms each fixed at one end thereof to chosen locations on the heart. Since all hearts are not identical and all paricardial spaces are not identical, some means must be provided to accommodate such variations between individual hearts. Therefore another form of the invention includes long, thin malleable heart supporting members which support the gross weight of the heart to hold it in the desired orientation, and fine immobilizing elements which gently support the heart without interfering with cardiac output. The gross weight support is provided by a clamp-like element that can be sized to accommodate an individual heart, and the other elements can be moved to account for the spacings and sizes for the particular heart being supported. In this manner, a heart, especially a beating heart, can be supported in the manner that is most effective for that particular heart. Thus, in the case of a beating heart, cardiac output can be maintained in an unabated and uninterrupted manner as there will be virtually no constrictions on the heart because the support will be perfectly fitted that particular heart.

A surgery target immobilizing element is fixed at one end thereof to a stationary element and has a heart-engaging element on the other end thereof. The heart-engaging element includes means for engaging the heart adjacent to the surgical target while leaving the target area exposed. A main support arm is fixed at one end thereof to a stationary element and to the cup-shaped element at the other end thereof. A vacuum can be applied to the cup-shaped element via the main support arm, and to heart-engaging elements on the ends of the support arms.

An alternative form of the retractor can be used in minimally invasive surgery. The alternative form includes a handle having a cup-shaped heart-engaging element on a distal end and a hand-grip on a proximal end thereof. The proximal end is located outside the patient during surgery. The alternative form also includes a cup-shaped element and a plurality of support arms, both rigid and flexible.

While this invention is disclosed in the preferred form for open chest procedures for beating heart surgery, it may also be utilized for minimally invasive procedures as well as those that use cardioplegia due to its novel time saving and enabling features. It is also noted that this disclosure is not directed to the art of anastomosis per se. However, it is directly related to enabling a surgeon to perform an anastomotic procedure in a precise and controlled manner.

The inventive device disclosed herein eliminates the need for use of the heart-lung machine. It allows a surgeon to lift and displace the heart to expose all vessels to regionally immobilize them for suturing without seriously impairing heart performance. Small support arms are attached around the heart so that even as the heart is lifted its shape is preserved. Since forces must be exerted to lift the heart, preference is made to lifting in such a way that the short axis (circular aspect) is maintained and allowed to shorten. The long axis can be used for more weight bearing since this will have relatively less effect on the performance of the heart.

Practically speaking, this means that the heart is attached at its apex (end of the long axis) and small support arms attach around the circumference of the heart. The support arms attach around the circumference of the heart. The support arms lift the heart and spread the support between the long and short axes of the heart. They are able to keep the heart in a circular shape and preserve its ability to contract. They can attach to at least one point on the circumference of the heart and/or at the apex and still lift and preserve the shape. The support arms on one side, most likely the bottom that gravity dictates, will be rigid support arms while the top support arms are flexible. This allows the circumference to be unrestricted so that there is virtually no impediment to shortening in the short axis. A pair of rigid support arms could attach around the circumference on each side of a target vessel to regionally immobilize that area for suturing. A separate stabilizer could be attached to the main support structure or come from a separate retractor base or come from the chest wall to stop movement at the surgical target area. The retractor of the present invention simulates pericardium support of the heart.

Once the stabilization of the beating heart has been achieved as with the retractor system of the present invention, it then becomes more feasible to entertain the idea of performing this surgery in a minimally invasive manner precluding the need for the median sternotomy.

BRIEF DESCRIPTION OF THE DRAWINGS FIGURES

FIGS. 6A and 6B illustrate the pumping action of a heart with the heart retractor in place.

FIGS. 7A and 7B illustrate two forms of a main support arm that can be used in conjunction with the heart retractor of the present invention.

DETAILED DESCRIPTION OF THE PREFERRED EMBODIMENT OF THE INVENTION

Figure 1:
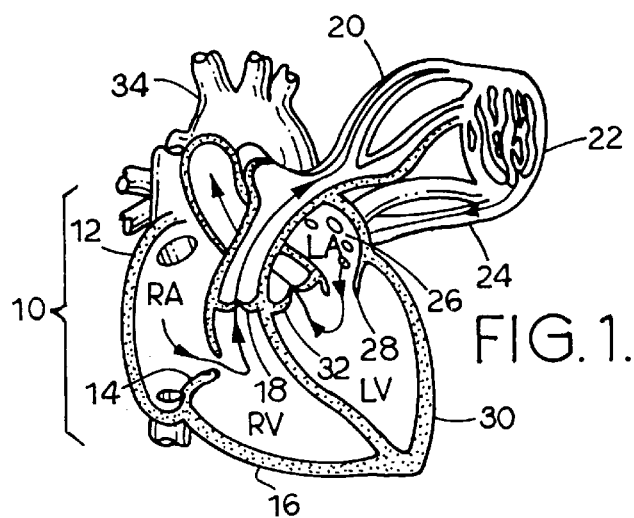
FIG. 1 illustrates blood flow in a normal heart.

In FIG. 1, the normal circulatory pattern of blood through heart 10 is illustrated. Blood from the venous system enters the first chamber of the heart, the right atrium (R.A.) 12. From right atrium 12, it passes through tricuspid valve 14 into right ventricle (R.V.) 16 and via pulmonic valve 18, enters pulmonary artery 20 which leads to lungs 22. In lungs 22, carbon dioxide is released and the blood is reoxygenated. Blood then exits lungs 22 back into pulmonary vein 24 which leads to left atrium (L.A.) 26. From left atrium 26, blood passes through mitral valve 28 into left ventricle (L.V.) 30. Blood then exits heart 10 via aortic valve 32 into aorta 34 and the generalized arterial circulation.

Cardiac contraction is orchestrated by electrical impulses originating from the heart's nervous system. Electrical stimulation to the myocardial fibers results in muscular contraction. Specifically timed electrical signals originating in the upper chambers of the heart cause the atriae to contract and empty blood into the ventricles 16 and 30. After atrial contraction, a short electrical delay takes place. This pause allows the ventricles 16 and 30 to receive blood from atriae before they are stimulated to contract. With ventricular contraction, blood is ejected from heart 10.

FIGS. 2A–2E illustrate a simplified diagram of normal cardiac contraction as visualized from left ventricle 30. The cardiac cycle can be broken down into two major stages: diastolic and systolic. Diastolic is the relaxation phase of the ventricular contraction cycle. During this time the ventricle relaxes and fills up with blood in preparation for the next contraction. Systole is the ventricular phase involved with contraction and the process of ejecting blood from the heart.

Figure 2A:
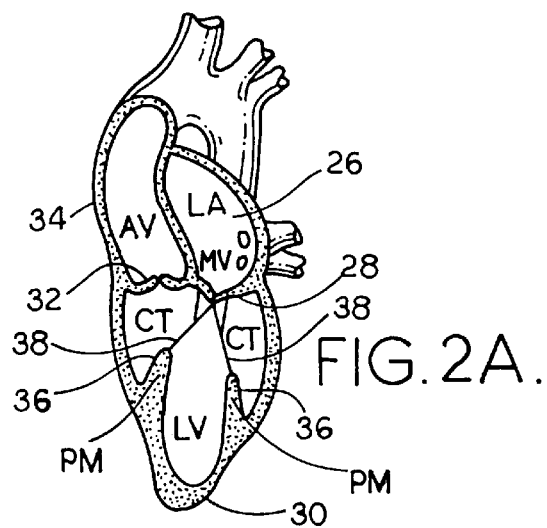
FIGS. 2A–2E illustrate the pumping action of a normal heart.

FIG. 2A illustrates the first phase of diastole which is isovolumetric relaxation immediately following a systolic contraction. This represents the transition phase between diastole and systole.

Figure 2B:
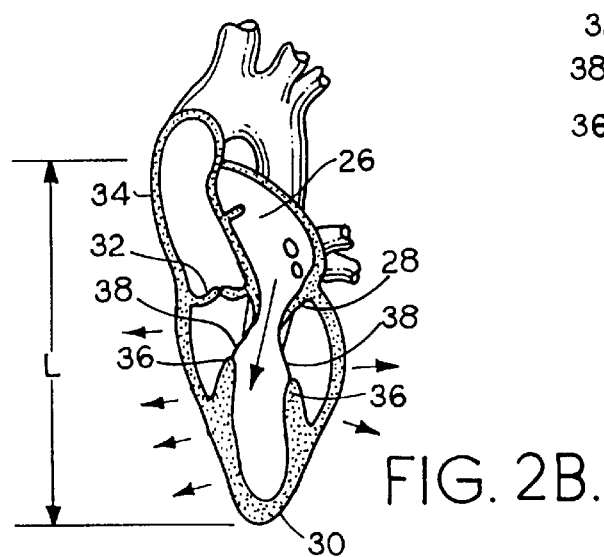

FIG. 2B illustrates that with further ventricular relaxation, a building of negative pressure within the ventricle due to dilation results in a rapid influx of blood. Additionally, the geometric angle formed between the ventricular wall, papillar muscle (P.M.) 36, chordac tendinea (C.T.) 38 and mitral valve (M.V.) 28 widens. This combined process results in the opening of mitral valve 28.

Figure 2C:
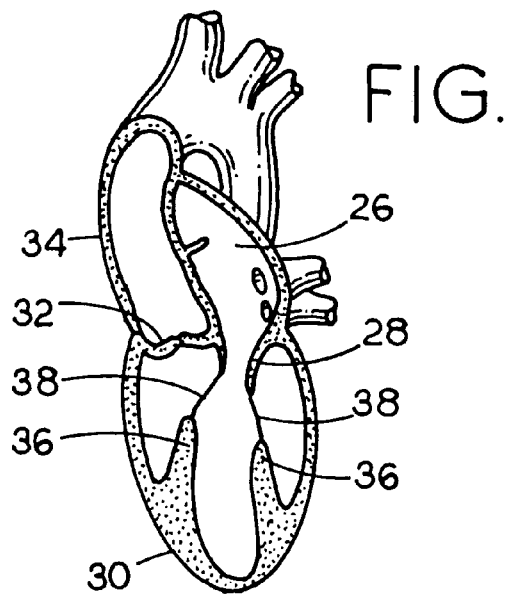

FIG. 2C illustrates the latter stages of diastolic ventricular filling. During this phase, left atrium 26 contracts to allow for maximal ventricular filling.

Figure 2D:
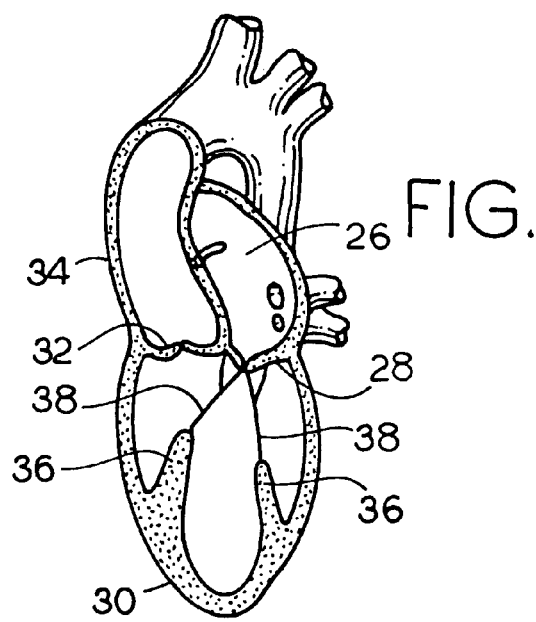

In FIG. 2D, left ventricle 30 begins to build muscular tension prior to actually contracting and secondarily reducing ventricular volume. This phase demonstrates isovolumetric contraction and is referred to as pre-systole. With building ventricular contraction, the intraventricular pressure increases which helps force mitral valve 28 closed. Additionally, the geometric relationship between the valve cusp and muscle-tendon supporting structures narrows with ventricular contraction which assists in mitral valve closure.

Figure 2E:
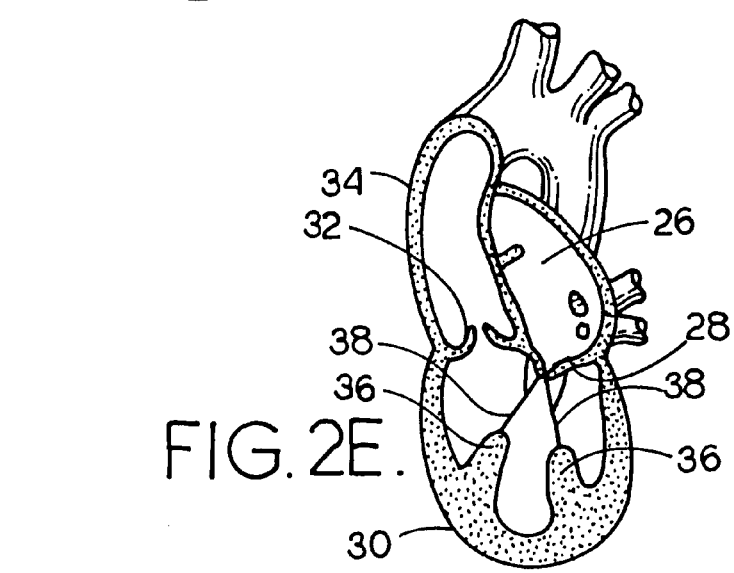

FIG. 2E illustrates that as ventricular contraction progresses, the intraventricular volume decreases and pressure builds. Once the ventricular pressure exceeds the blood pressure within aorta 34, aortic valve (A.V.) 32 is pushed open. Blood is then ejected from the ventricular cavity into aorta 34. This phase is called systole.

By comparing the figures, it can be seen that the overall length of the heart, as illustrated by dimension L, changes little throughout the process. Therefore, if the heart is clamped in a manner that restricts the length dimension while permitting the other dimensions to change, the operation of the heart will not be inhibited. It is this feature that the inventors have taken advantage of to develop a heart retractor that can be used on a beating heart. By immobilizing the heart in a direction along dimension L, but allowing the remainder of the heart to operate in a normal manner, operation of the heart is not restricted. The retractor of the present invention further immobilizes only the specific surgery target area whereby the remainder of the heart operates in an unrestricted manner. Thus, only the specific surgery location is immobilized. This is all that is required for a successful surgery and the entire heart need not be immobilized. The heart retractor of the present invention also lifts the heart in a manner that permits unrestricted operation of the heart as well.

Figure 3:
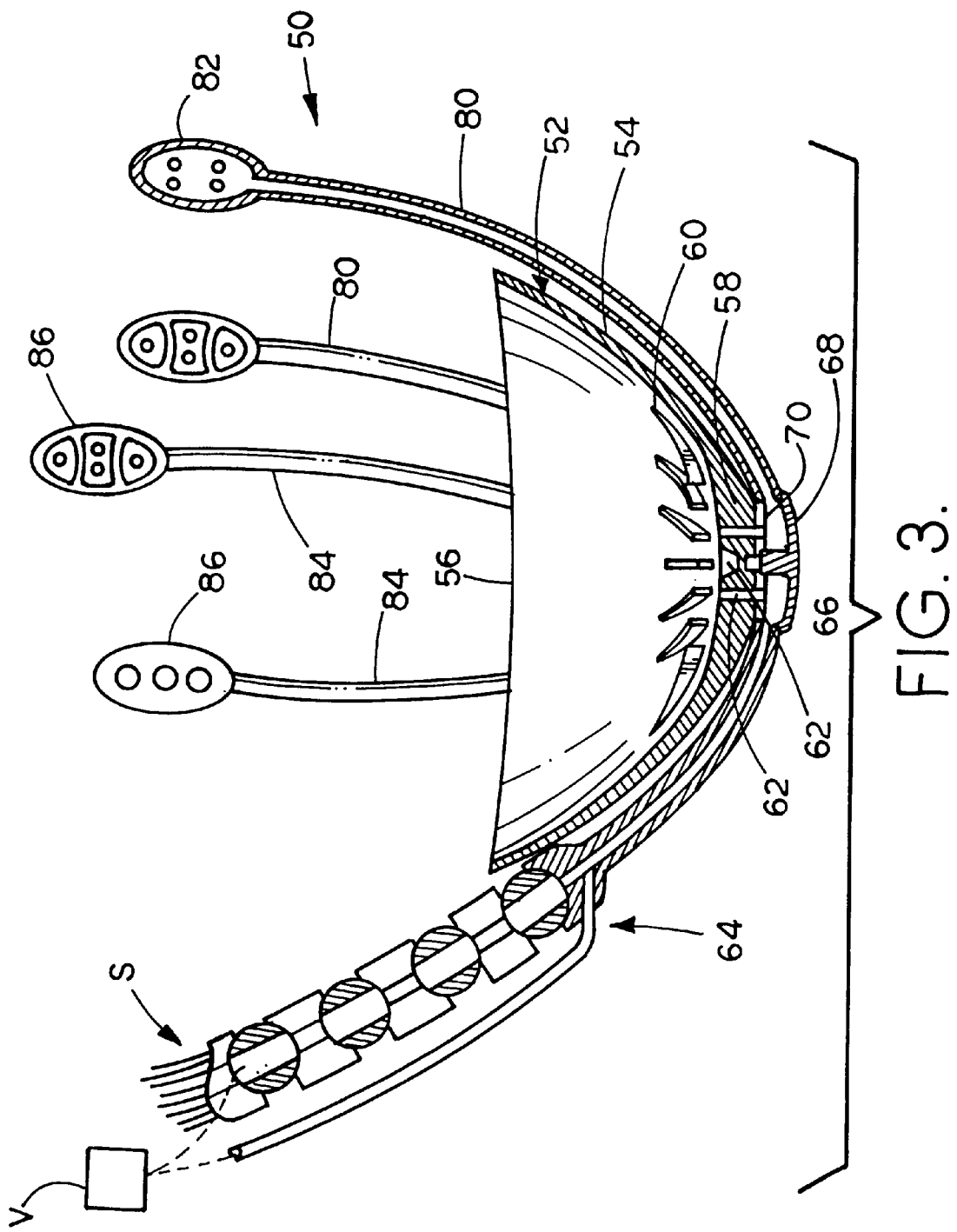
FIG. 3 is a sectional elevational view of a heart retractor embodying the present invention.
Figure 4:
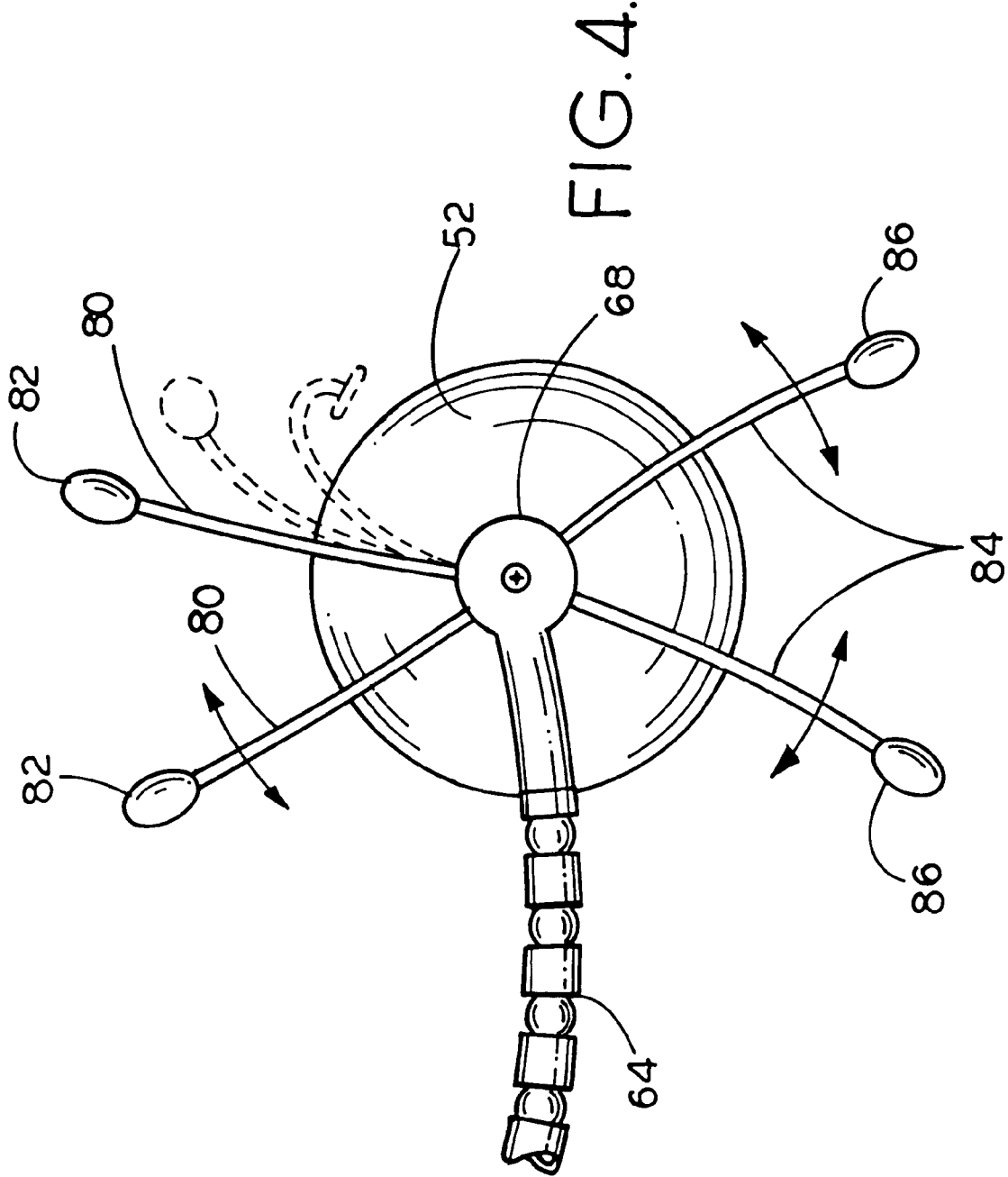
FIG. 4 is a bottom view of the heart retractor.
Figure 5:
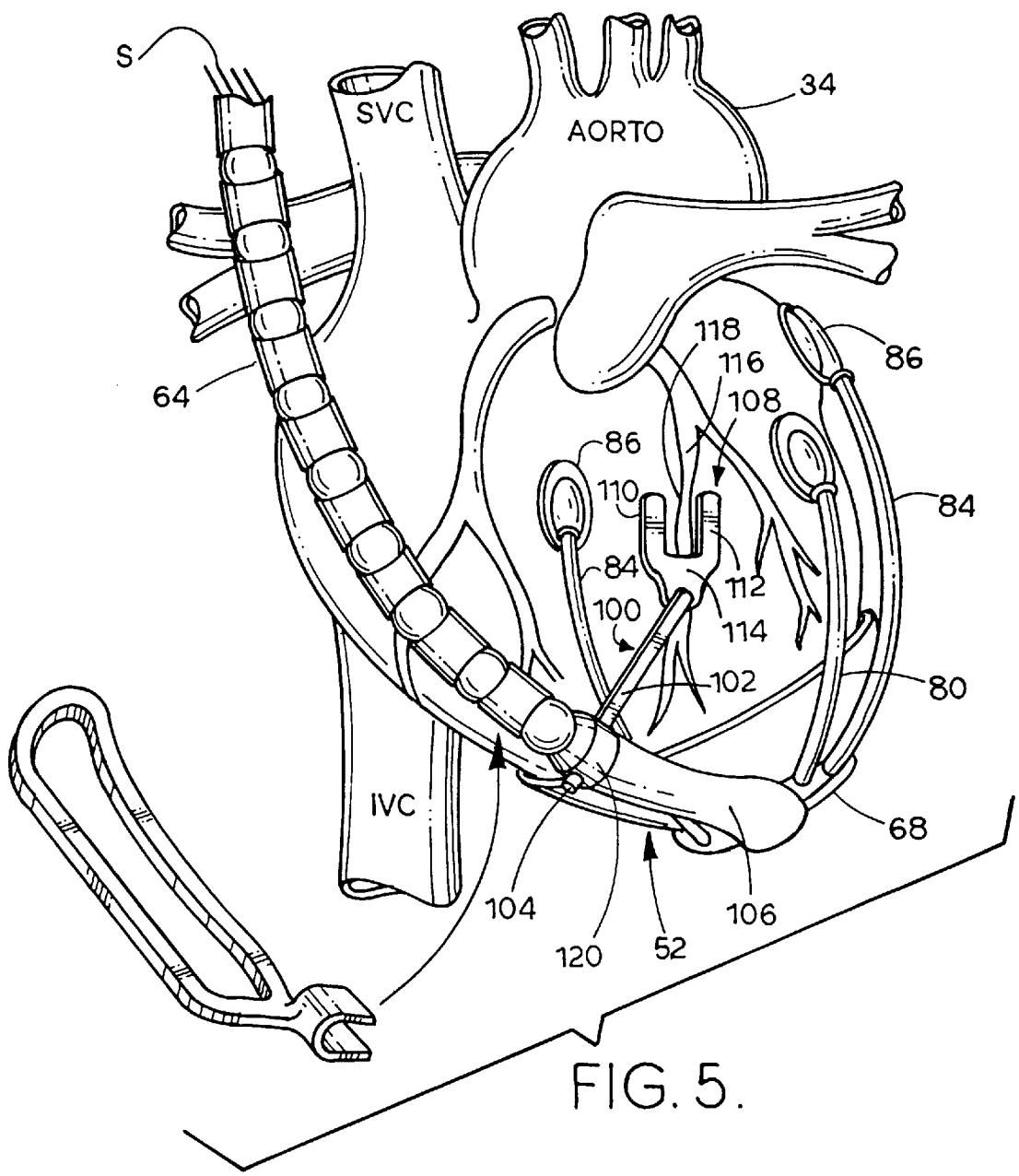
FIG. 5 is a perspective view of a heart retractor in place on a heart.

Referring specifically to FIGS. 3–5, heart retractor 50 of the present invention is shown in detail. The retractor permits regional and specific immobilization of the heart while permitting essentially unabated cardiac output whereby all coronary arteries, including the circumflex coronary artery, to be bypassed and the heart maintained in an unnatural position and/or orientation. The retractor includes a gross support means 52 for engaging an apex portion (gross weight) of a heart to support the heart when the heart is lifted for surgery. Support means 52 includes a cup-shaped portion 54 having a top rim 56 and an apex 58 with ribs 60 defined adjacent to the apex to support the heart in the cup-shaped element. While a cup-shaped element is preferred, one could substitute other attachment configurations without departing from the scope of this disclosure. The only requirement is that the element be sized and shaped to adequately support the heart to achieve the results discussed herein, to wit: supporting the heart in an orientation suitable for the type of heart surgery of interest here. Thus, no limitation as to specific shape is intended for element 52. Vacuum ports 62 are defined through the cup-shaped element at apex 58 to be fluidically connected with a vacuum source for securing the heart in place in the cup-shaped element. A vacuum source V is fluidically connected to holes 62 via main support arm 64 which has one end thereof fixed to a stationary support S (see FIG. 5), such as the operating table, or a rib spreader, and the other end thereof attached to the cup-shaped element via fastener 66 attached to anchor 68. A manifold-like portion 70 of the cup-shaped element distributes the vacuum to the various ports, such as ports 62 to be applied to secure retractor 50 to the heart. An alternative form of the retractor includes a separate hose 72 to transfer vacuum to the manifold 70. Ribs 60 keep heart fat from clogging the vacuum manifold section.

Retractor 10 further includes a fine support means for immobilizing selected portions of the heart while permitting non-immobilized portions to move in a manner that continues heart operation. This fine support means includes a plurality of rigid arms 80 each being fixed at one end thereof to anchor 68 and having a heart-attaching element 82 thereon, such as at the outer end thereof. As used herein, the term "rigid" is a relative term and means that the arms are rigid enough whereby the force of the heart won't move them. But they can be adjustable such as being formed of a wire-wound gooseneck or soft metal which allows each arm to be individually shaped according to the needs of the attachment location. The heart-attaching elements can be suction attachment points, such as suction cups that are fluidically connected to manifold 70. Other means of attaching the elements to the heart, can be used as well without departing from the scope of the present disclosure as will occur to those skilled in the art based on the teaching of this disclosure. Examples of other such elements include glue, sutures, clamps, shallow pins, pincers or the like, with attachment points being located on the arm as suitable. The rigid arms secure small or fine areas of the heart in place with respect to gross element 52 while permitting the heart to move as required to continue unabated cardiac output. Support means 50 further includes a plurality of flexible support arms 84 each fixed at one end thereof to anchor 68 and having a heart-attaching element 86 on the outer end thereof. Elements 86 can be suction elements similar to the just-discussed elements 82. Flexible arms 84 can be adjusted to secure the heart in the most advantageous locations whereby the heart can continue to operate without undue restriction.

The rigid support arms can be located on one side of the heart so the heart can beat "away" from the rigid support arms as is best indicated in FIGS. 6A and 6B. One "side" of the heart is fixed, however, the other "side" is free to move with respect to the fixed side. In this manner, the heart can continue to operate in its normal manner. As shown, by way of example, in FIG. 6A, "side" A is fixed by the rigid support arms, while "side" B is free to move relative to "side" A. Thus, by comparing FIGS. 6A and 6B, it can be seen that "side" B moves toward "side" A from FIG. 6A to FIG. 6B. Thus, while "side" A is fixed, "side" B moves to permit continued operation of the heart even though it is fully and securely supported by retractor 10. Blood flow is indicated in FIG. 6B by arrow 88.

Therefore, broadly, the overall retractor comprises a main support which includes the arms, a hub and a stationary member, such as a table top, the floor or the like; a gross support which includes the apex cup and fine support means which regionally immobilizes portions of the heart while leaving other regions of the heart free to operate in an unabated manner to maintain heart output during the surgical procedure. The fine support means can include the rigid arms as well as the surgery target immobilizing means. In this manner, the heart is supported regionally yet operates to maintain blood flow during coronary surgery.

Figure 7B:
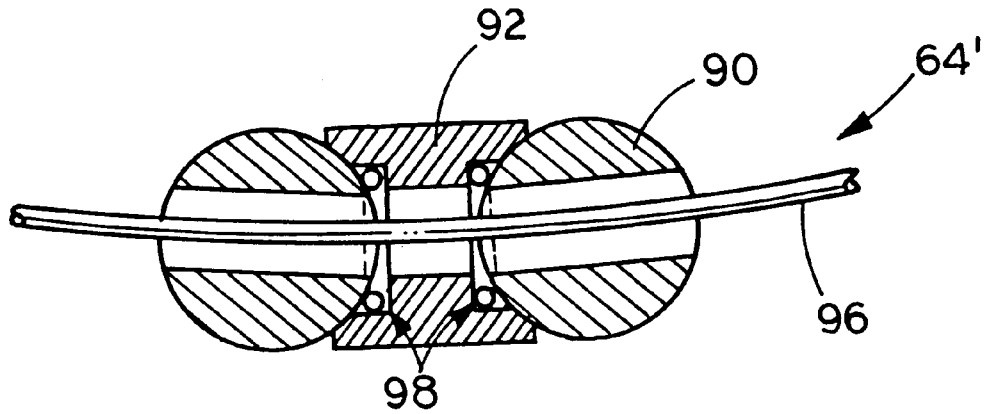

FIGS. 7A and 7B show alternative forms of the main support arm as including spherical links 90 and tubular links 92 that surround a vacuum supply hose 94 and a tension cable 96. Hose 64' includes O-ring seals 98 and the tension cable. The tension cables are operated to make the main support arm rigid. Until the tension cable is pulled taught, the main support arm is flexible and can be moved into the desired position and orientation with the links 90 and 92 acting like locks to permit the cables to be moved into position and then locked in position. Once there, the tension cable is tightened and the main support arm becomes rigid.

Referring to FIG. 5, it can be seen that retractor 10 includes a surgery target-immobilizing element 100 for immobilizing that exact location of the heart on which surgery is being performed. Element 100 includes a rigid arm 102 fixed at one end 104 to connecting arm 106 of stationary main arm 64 and having a U-shaped target-defining element 108 on the other end. Element 108 includes two legs 110 and 112 connected by a central section 114. As shown in FIG. 5, the target vein 116 being incised at 118 is located between legs 110 and 112. Element 108 is rigid as is arm 102 so target area 118 will be immobile even though the remainder of the heart adjacent to this area will be moving. However, only a small section of the heart will be immobilized and thus should not affect the overall operation of the heart during the operation. The target-immobilizing element can be moved anywhere it is needed by simply loosening clamp 120 and moving arm 102 as necessary.

Figure 8:
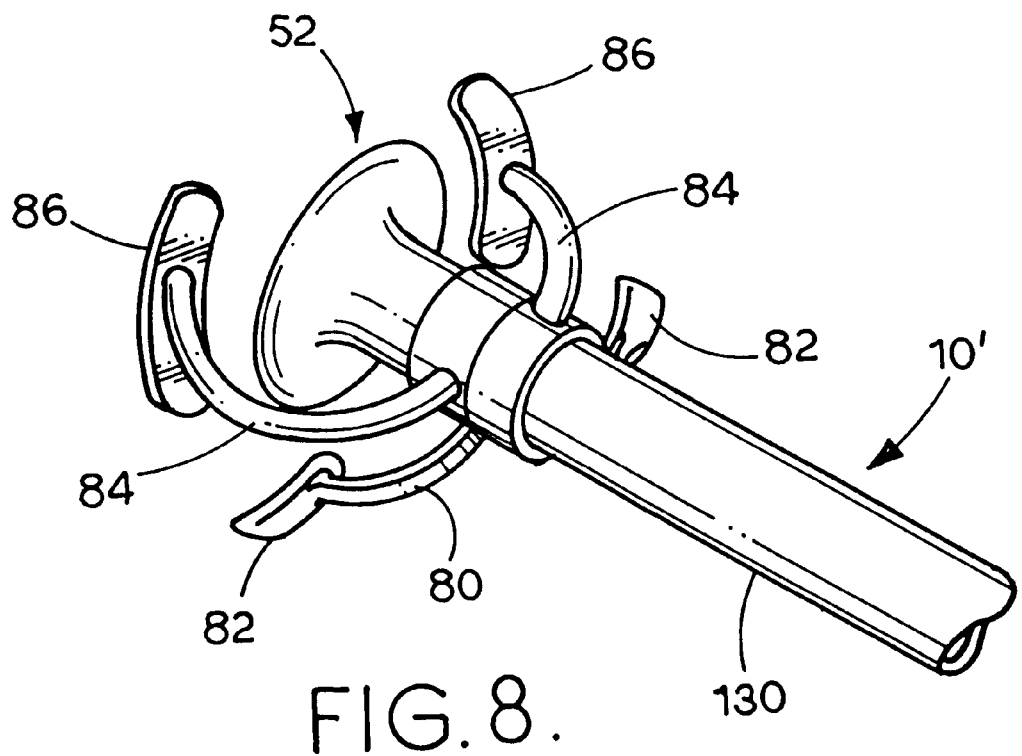
FIG. 8 is a perspective view of an alternative form of the heart retractor of the present invention that can be used in minimally invasive surgery.
Figure 9:
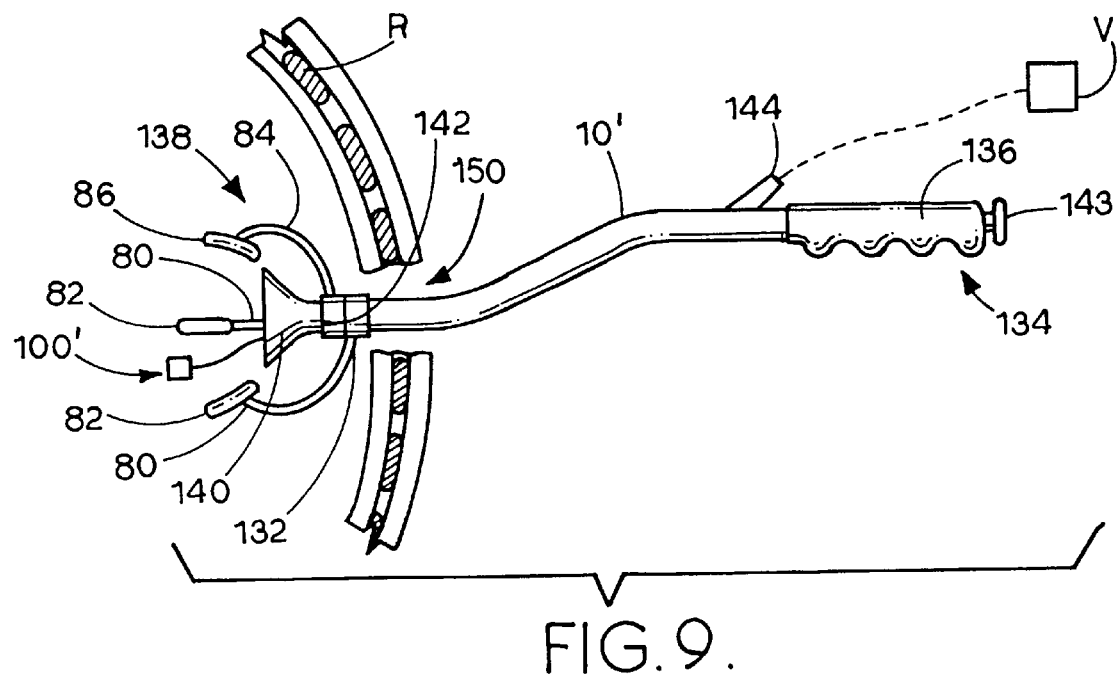
FIG. 9 is an elevational view of the FIG. 8 form illustrating the use thereof.
Figure 10:
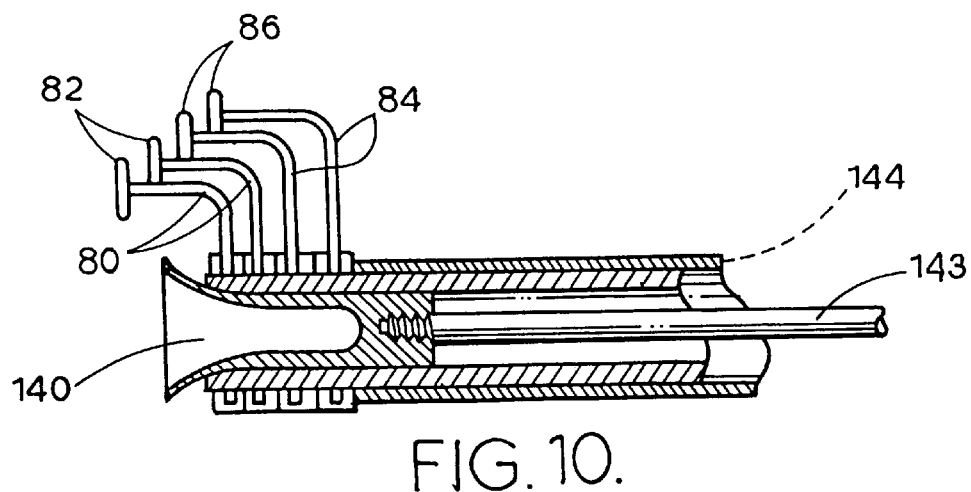
FIG. 10 shows the FIG. 8 form retracted into the handle of the tool.

An alternative form of the retractor is disclosed in FIGS. 8–10 and is used for minimally invasive surgery. Retractor 10' includes a rigid handle 130 having a distal end 132 and proximal end 134 with a hand-grip 136 on the proximal end and a heart support means 138 on the distal end. Heart supporting means 138 includes a cup-shaped heart support element 140 fixed at an apex 142 thereof to the handle by a rod 143 (see FIG. 10) to be in position to engage the apex section of a heart. Means 138 further includes a plurality of rigid arms 80' and a plurality of flexible arms 84' each of which is attached at one end thereof to the handle and having a heart-engaging element 82 or 86 at the other end thereof. Means 138 is similar to means 50 and thus will not be discussed in detail except to note that elements 82 and 86 can be suction elements connected to a source of vacuum V' via a conduit located inside handle 130 and having a vacuum connection 144. Means 138 operates in the same manner as means 50 and thus will not be further discussed. It is noted that the elements 82, 86, 82' and 86' could include screen mesh to ensure that loose fat from the heart does not become entrapped in the suction tubing at the exit point of the element. A surgery target immobilizing element 100' similar to the above-discussed element 100 can also be included in retractor 10' and will operate and function in a manner similar to element 100 and thus will not be further discussed.

Retractor 10' is inserted through a minimally invasive port 150 defined in a patient between ribs R and manipulated as necessary to engage and support a heart.

Retractor 10' is shown in FIG. 10 in a position that permits insertion thereof into a patient. As shown in FIG. 10, cup-shaped heart support element 140 is flexible and is retracted into the hollow handle 144 for insertion and/or removal. The element 140 is moved into and out of the handle by moving rod 143 which has an end thereof located adjacent to handle 134 as shown in FIG. 9.

As was discussed above, during operation of the heart, the left ventricle is a conical shaped cavity narrowest at the apex. It shortens both in length and in diameter during a pumping stroke (contraction). Since the volume of blood displaced is more dependent on the reduction in diameter (square) than the shortening in length (first power), any measure which reduces the diameter of shortening is very detrimental. Also, the right ventricle is attached to the left ventricle and is considerably thinner and less powerful. Suction attachments to this part of the heart which would impede the shortening of muscle may be poorly tolerated. The invention disclosed and taught herein uses a series of linked attachments to the heart. Attachments which are near the artery to be bypassed are paired on opposite sides of the artery and do not move—they immobilize the artery and therefore the muscle in the target region. A lifting suction is applied at the apex of the heart. If this were the only site of lifting, the heart would be stretched and there would be no diameter left. Thus, no blood could be ejected. However, this invention adds additional heart attaching elements that are attached to the heart to lift it. These attachment points would be mobile in that they could allow the heart to move inward and reduce the diameter and eject blood. The key to the invention is the linking of lifting (both at the apex and around the circumference of the heart) and regional immobilization which stops one part around the circumference from moving and therefore allows easy suturing.

As discussed above, it could be important in some cases to account for variations between individual hearts. A retractor 10A shown in FIGS. 11–15 is adjustable so it can be sized and shaped to account for variations in heart size and shape as well as paracardial spacings. Retractor 10A includes a gross weight support means 200 and fine support means 202, all supported by a main support means 204, such as an adjustable arm that is mounted at one end thereof to a stationary element.

Figure 11:
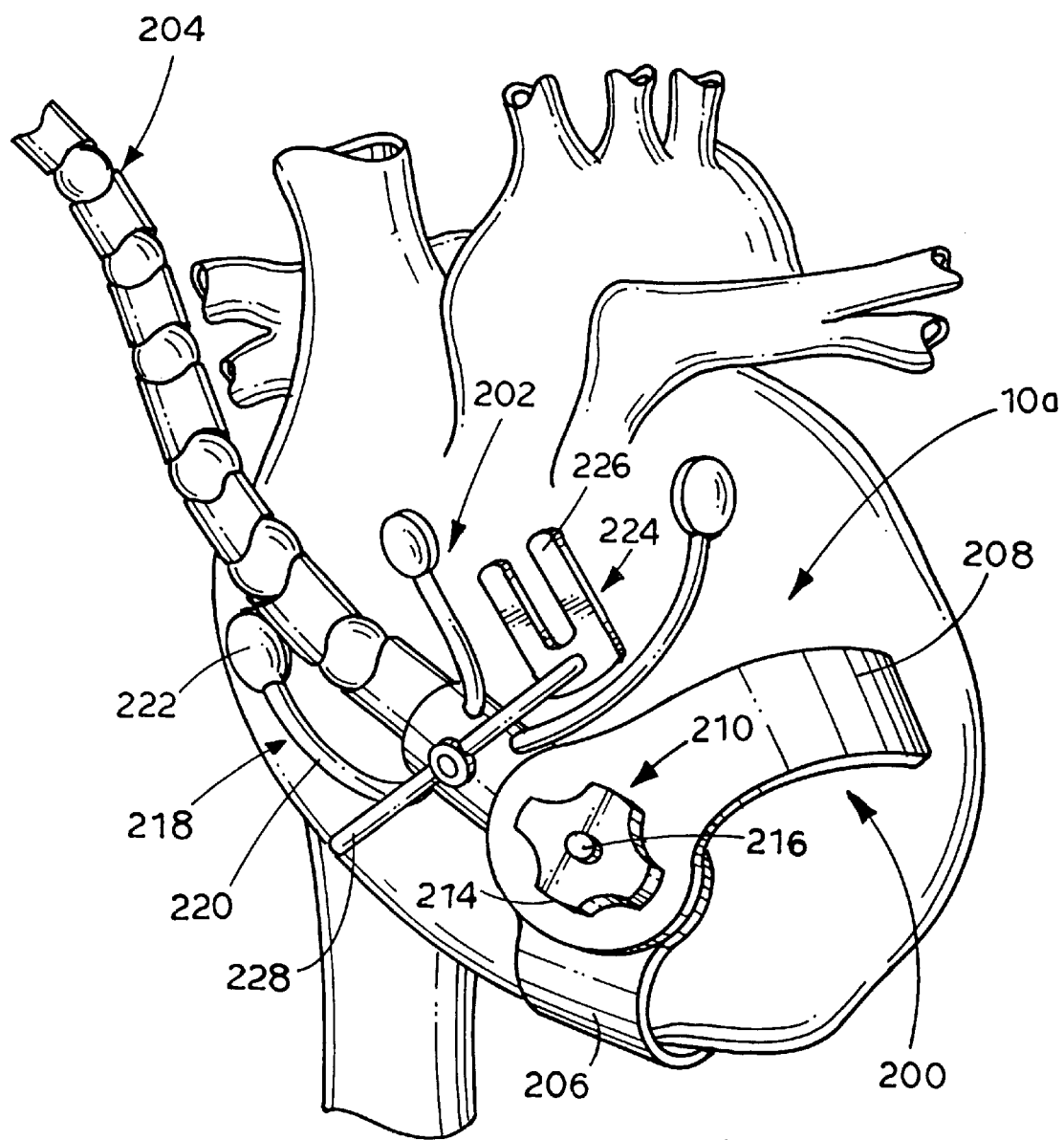
FIG. 11 shows a tool that can support a beating heart and which can be sized and shaped to accomodate the particular heart being supported.
Figure 12:
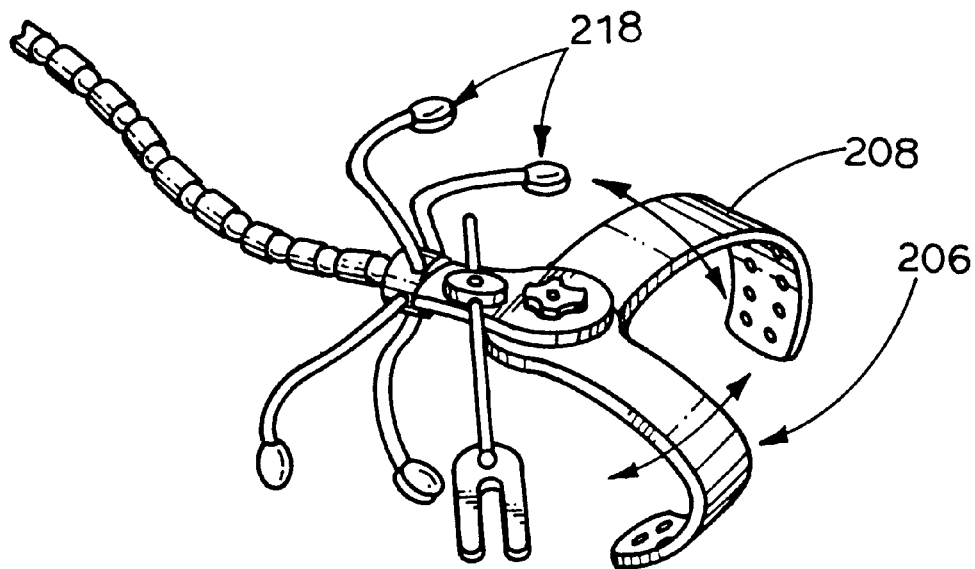
FIG. 12 shows the FIG. 11 retractor in another configuration.
Figure 13:
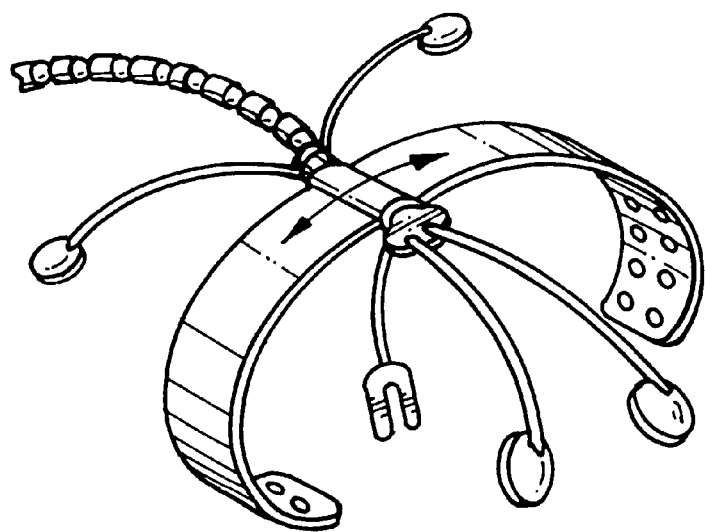
FIG. 13 shows the FIG. 11 retractor in yet a third configuration.
Figure 14:
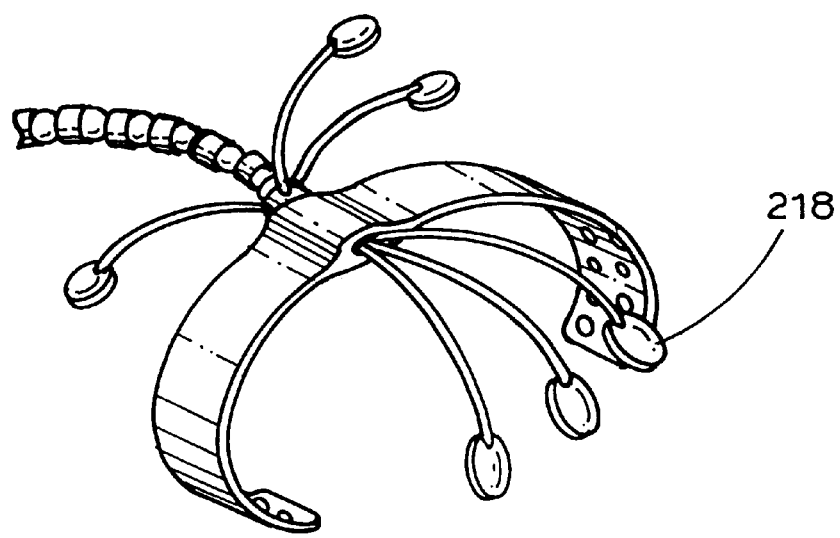
FIG. 14 shows a retractor similar to FIG. 11 but with additional fine support arms.

Gross weight support means 200 includes two wings 206 and 208 which are adjustably connected together at their proximal ends by a fastener 210. Fastener 210 includes a hub 212 that frictionally engages the wings. A hand wheel 214 is threaded onto a fastener 216 to tighten the hub against the wings to hold the wings in a desired position. The wings can move from an angular orientation, such as shown in FIGS. 11 and 12 to a linear orientation such as shown in FIGS. 13 and 14. Retractor 10A is engaged against a heart, and wings 206 and 208 are adjusted to most efficiently support the gross weight of the heart and the hand wheel is tightend down.

Figure 15:
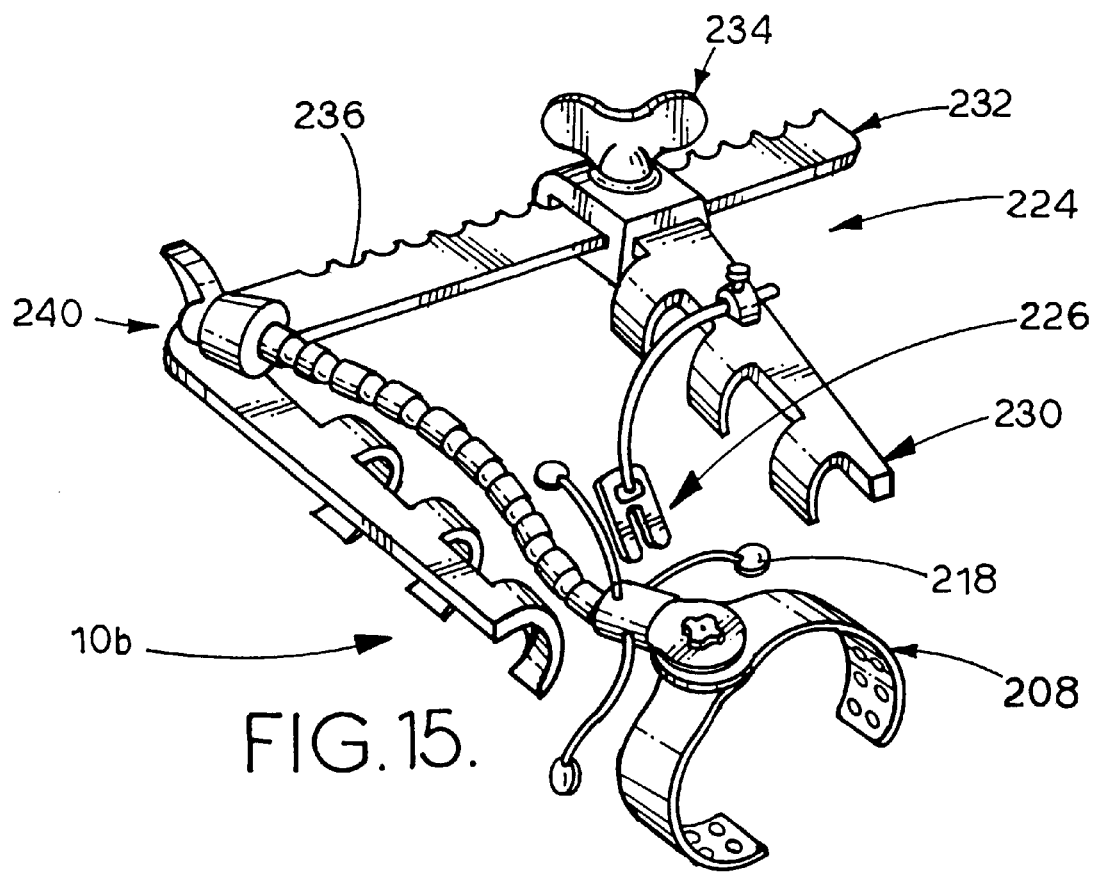
FIG. 15 shows yet another form of retractor in which a target immobilizing element is attached to an adjustable arm.

Regional support of the heart is provided by means 202 which includes fine support elements, such as element 218 having a malleable arm 220 and an element 222 attached to the heart, such as by suction, as well as a target immobilizing means 224. Target immobilizing means includes a U-shaped heart engaging element 226 attached to a support rod 228 that is mounted on the main support means, such as on arm 204. Retractor 10A has rod 208 mounted near hub 210; however, other forms of the retractor, such as retractor 10B shown in FIG. 15, can have the rod mounted in any convenient location. As shown in FIG. 15, target immobilizing means 224' includes a sternal retractor 230 connected to an arm 232 by a wing nut fastener 234. Arm 232 has a knurled edge 236 for holding retractor 230 in the chosen position. As shown in FIG. 15, target immobilizing means is mounted on sternal retractor and is thus mounted on the main support means via the sternal retractor. A lock means 240 attaches the sternal retractor to the main support arm.

It is understood that while certain forms of the present invention have been illustrated and described herein, it is not to be limited to the specific forms or arrangements of parts described and shown.

We claim:

1. A retractor for use in heart surgery comprising:
   a rigid gross support means for engaging a heart to support the heart when the heart is oriented for surgery and including a multipositional support element fixed to a stationary support;
   means for immobilizing selected portions of the heart while permitting non-immobilized portions to move in a manner that continues heart operation; and
   a surgery target immobilizing means connected to said support element and engaging the heart adjacent to a surgery target for immobilizing the heart at and immediately adjacent to the surgery target
   whereby the heart is supported and free to operate during surgery while being locally immobilized at the surgery target.

2. The heart retractor defined in claim 1 wherein said gross support means includes a cup-shaped element for engaging and supporting the heart adjacent to the apex section of the heart.

3. The heart retractor defined in claim 2 wherein said support means further includes a plurality of rigid support arms each connected at one end thereof to said stationary support element and having a heart-attaching element thereon.

4. The heart retractor defined in claim 3 wherein said each heart-attaching element includes a suction attachment point.

5. The heart retractor defined in claim 3 wherein said support means further includes a vacuum source and means fluidically connecting said vacuum source to said cup-shaped element and further including means fluidically connecting said vacuum source to each heart-attaching element.

6. The heart retractor defined in claim 2 wherein said support means further includes a vacuum source and means fluidically connecting said vacuum source to said cup-shaped element.

7. The heart retractor defined in claim 1 wherein said target-immobilizing element includes a U-shaped target-defining element having two legs and means thereon for engaging the heart to position one leg on each side of the surgery target.

8. The heart retractor defined in claim 7 wherein said target-immobilizing element further includes a rigid arm attached to said U-shaped element and to said stationary support element.

9. The heart retractor defined in claim 1 wherein said means for immobilizing selected portions of the heart includes attachment means thereon for attaching to the surface of the heart.

10. A heart retractor for use in heart surgery comprising:
   support means for supporting the gross weight of a heart to support the heart when the heart is oriented for surgery and including a main support arm having means at one end thereof for mounting the support arm on a stationary support; and
   means for immobilizing selected portions of the heart and permitting other sections to move as required to continue heart operation during surgery, said immobilizing means including at least one rigid support arm connected at one end thereof to said support means and having means thereon for releasably attaching said rigid support arm to the heart, and at least one flexible support arm connected at one end thereof to said support means and having means on another end thereof for releasably attaching said flexible support arm to the heart.

11. The heart retractor defined in claim 10 wherein said means for immobilizing selected portions of the heart includes a plurality of flexible arms each connected at one end thereof to said support means and each having a heart-engaging member thereon.

12. The heart retractor defined in claim 11 wherein each heart-engaging member is a suction attachment point.

13. The heart retractor defined in claim 2 further including a surgery target immobilizing element having one end thereof connected to said support means and heart-engaging elements on another end thereof.

14. A retractor for use in minimally invasive heart surgery comprising:
   support means for engaging a heart to support the heart when the heart is oriented for surgery and including a handle having a distal end and a proximal end, said proximal end being located outside of a patient during surgery, a support element fixed to said distal end, and rigid elements fixed to said distal end and engaging and supporting chosen sections of the heart; and
   means for immobilizing selected portions of the heart while permitting non-immobilized portions to move in a manner that continues heart operation
   whereby the heart is supported and free to operate during minimally invasive surgery while being immobilized at selected locations.

15. The retractor defined in claim 14 wherein said means for immobilizing selected portions of the heart includes a plurality of flexible arms each connected to said handle.

16. The retractor defined in claim 15 wherein each rigid element includes a heart-engaging element and further includes a vacuum source fluidically connected to each heart-engaging element.

17. The retractor defined in claim 14 wherein said support means includes a cup-shaped element fixed to the distal end of said handle.

18. The retractor defined in claim 17 further including a vacuum source fluidically connected to said cup-shaped element.

19. A retractor for use in heart surgery comprising:
   support means for engaging a heart to support the heart when the heart is oriented for surgery and including a support element fixed to a stationary support and rigid elements engaging and supporting chosen sections of the heart;
   means for immobilizing selected portions of the heart while permitting non-immobilized portions to move in a manner that continues heart operation
   whereby the heart is supported and free to operate during surgery while being locally immobilized at the surgery target.

20. A heart positioning device for use in cardiac surgery comprising:
   support means for engaging a heart to support the heart when the heart has been oriented into an unnatural position or orientation for coronary surgery;
   means for attaching said support means to the heart so the heart operates with uncompromised ventricular function when the heart is oriented into an unnatural position or orientation for coronary surgery:
   means engaging sections of the heart to immobilize the sections engaged while permitting non-engaged sections of the heart to move in a manner whereby essentially unabated cardiac output is maintained during surgery while the heart is regionally immobilized.

21. The heart retractor defined in claim 20 wherein said support means includes a means for engaging the heart sufficiently to support the heart during coronary surgery.

22. The heart retractor defined in claim 20 wherein said support means includes arms which have locking elements for permitting the arms to be moved into position and then locked in position.

23. The heart retractor defined in claim 20 further including a surgery target immobilizing element connected to said support means and engaging the heart adjacent to a surgery target for immobilizing the heart at and immediately adjacent to the surgery target.

24. A heart retractor for use in heart surgery comprising:
   support means for engaging an apex portion of a heart to support the heart when the heart is lifted for surgery and including a main support arm having means at one end thereof for mounting the support arm on a stationary support; and
   means for immobilizing selected portions of the heart and permitting other sections to move as required to continue heart operation during surgery, said immobilizing means including at least one rigid support arm connected at one end thereof to said support means and having means on another end thereof for releasably attaching said rigid support arm to the heart, at least one flexible support arm connected at one end thereof to said support means and having means thereon for releasably attaching said flexible support art to the heart.

25. The heart retractor defined in claim 24 further including a surgery target immobilizing element having one end thereof connected to said support means and heart-engaging elements thereon.

26. A retractor for use in heart surgery comprising:
   a main support;
   a gross support means for engaging a heart and supporting the heart when the heart is oriented for surgery, said gross support means being attached to said main support;
   a fine support means for supporting portions of the heart during surgery, said fine support means being attached to said gross support means with non-supported portions of the heart moving in a manner whereby essentially unabated cardiac output is maintained during surgery while the heart is regionally immobilized at supported portions and including rigid elements engaging and supporting chosen sections of the heart.

27. A retractor for use in heart surgery comprising:

a main support;

a gross support means for engaging a heart and supporting the heart when the heart is oriented for surgery, said gross support means being attached to said main support and including means for adjusting the shape of said gross support means;

a fine support means for supporting portions of the heart during surgery, said fine support means being attached to said gross support means with non-supported portions of the heart moving in a manner whereby essentially unabated cardiac output is maintained during surgery while the heart is regionally immobilized at supported portions and including rigid elements engaging and supporting chosen sections of the heart.

28. The retractor defined in claim 27 wherein said means for adjusting the shape of said gross support means includes a fastener attaching two arms together, with said two arms engaging the heart to support the gross weight of the heart.

29. The retractor defined in claim 27 further including attachment means on said fine support means for contacting the heart.

30. The retractor defined in claim 29 wherein said attachment means include suction points.

31. The retractor defined in claim 27 further including a support arm and a surgery target immobilizing element attached to said support arm.

32. A heart positioning device for use in cardiac surgery comprising:

a stationary support;

a rigid arm connected to said stationary support;

a flexible element connected to said rigid arm;

means on said flexible element for releasably attaching said flexible element to a heart to orient the heart into an unnatural position or orientation for coronary surgery and so the heart operates with uncompromised ventricular function when oriented into the unnatural position or orientation during coronary surgery.

33. The heart positioning device defined in claim 32 further including a second flexible element connected to said rigid arm.

34. The heart positioning device defined in claim 32 wherein said rigid arm is multipositional.

35. A heart positioning device for use in cardiac surgery comprising:

a stationary support for orienting the heart into an unnatural position or orientation for coronary surgery;

a flexible element connected to said stationary support for supporting the heart in a manner so the heart operates with uncompromised ventricular function when the heart is oriented into the unnatural position during coronary surgery; and means on said flexible element for releasably attaching said flexible element to the heart.

36. A heart positioning device for use in cardiac surgery comprising:

a stationary support for orienting the heart into an unnatural position or orientation for coronary surgery;

a rigid arm connected to said stationary support;

a flexible element connected to said stationary support;

means on said flexible element for releasably attaching said flexible element to a heart in a manner so the heart operates with uncompromised ventricular function when the heart is oriented into the unnatural position during coronary surgery.

37. The heart positioning device defined in claim 36 further including a second flexible element connected to said rigid arm.

38. The heart positioning device defined in claim 36 wherein said stationary support is multipositional.

39. A heart positioning device for use in cardiac surgery comprising:

a frame;

a stationary support attached to said frame for orienting the heart into an unnatural position or orientation for coronary surgery;

a flexible element connected to said stationary support for supporting the heart in a manner so the heart operates with uncompromised ventricular function when the heart is oriented into the unnatural position during coronary surgery; and means on said flexible element for releasably attaching said flexible element to the heart.

40. The heart positioning device defined in claim 39 further including a second flexible element connected to said stationary support.

41. A heart positioning device for use in cardiac surgery comprising:

a stationary support;

a flexible element connected to said stationary support for supporting a heart in a manner so the heart operates with uncompromised ventricular function when the heart is oriented into an unnatural position or orientation during coronary surgery; and means on said flexible element for releasably attaching said flexible element to the heart.

42. The device defined in claim 41 wherein said stationary support is multipositional for allowing the stationary support to move in a plurality of orientations and positions.

* * * * *